US008830307B2

(12) United States Patent
Hirakawa

(10) Patent No.: US 8,830,307 B2
(45) Date of Patent: Sep. 9, 2014

(54) IMAGE DISPLAY APPARATUS

(75) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 1279 days.

(21) Appl. No.: 11/631,273

(22) PCT Filed: Feb. 2, 2006

(86) PCT No.: PCT/JP2006/301795
§ 371 (c)(1),
(2), (4) Date: May 7, 2007

(87) PCT Pub. No.: WO2006/123455
PCT Pub. Date: Nov. 23, 2006

(65) Prior Publication Data
US 2008/0212881 A1 Sep. 4, 2008

(30) Foreign Application Priority Data

May 20, 2005 (JP) ................................. 2005-148670

(51) Int. Cl.
A62B 1/04 (2006.01)
A61B 1/00 (2006.01)
G06T 7/00 (2006.01)
A61B 1/04 (2006.01)

(52) U.S. Cl.
CPC .............. *A61B 1/042* (2013.01); *A61B 1/00045* (2013.01); *G06T 2207/10068* (2013.01); *A61B 1/0005* (2013.01); *G06T 7/0012* (2013.01); *G06T 7/0028* (2013.01); *G06T 2207/30092* (2013.01); *G06T 7/0026* (2013.01); *G06T 2207/30028* (2013.01)
USPC ............... 348/65; 348/45; 382/128; 382/190; 382/195; 382/224; 382/225; 382/243

(58) Field of Classification Search
CPC .... A61B 1/00045; A61B 1/041; A61B 1/005; G06T 2207/10068; G06T 7/0012; G06T 7/0026; G06T 7/0028
USPC .............. 348/65, 45; 382/128, 190, 195, 224, 382/225, 243
See application file for complete search history.

(56) References Cited

U.S. PATENT DOCUMENTS
6,487,360 B1 * 11/2002 Sumiyoshi et al. ........... 386/282
(Continued)

FOREIGN PATENT DOCUMENTS
JP 2001-359039 12/2001
(Continued)

OTHER PUBLICATIONS
Abstract of International Publication No. WO 01/87377 A2.
(Continued)

*Primary Examiner* — Oleg Survillo
(74) *Attorney, Agent, or Firm* — Scully, Scott, Murphy & Presser, P.C.

(57) ABSTRACT

To reduce a display time of an image for which an observation is less required, and to effectively perform an observation of a series of images, the image display apparatus (1) includes an image processing controller (2a) that acquires an image from a storage unit (5), controls various image processes for the acquired image, and stores an image of a processing result in the storage unit (5), an image classification unit (2b) that calculates a correlation value between temporally continuous images and classifies each of the images into an image group based on the calculated correlation value, an image-of-interest detecting unit (2c) that detects a feature-image area including a predetermined feature from each of the images, and detects the feature image including the detected feature-image area as an image-of-interest, a representative-image extracting unit (2d) that extracts the image-of-interest and a first image in each of the image groups as a representative image and sets a display rate for each of the extracted representative images, and an image display controller (6a) that performs a control of sequentially displaying the series of representative images based on the set display rates.

6 Claims, 14 Drawing Sheets

(56) References Cited

U.S. PATENT DOCUMENTS

| | | | |
|---|---|---|---|
| 6,709,387 B1 * | 3/2004 | Glukhovsky et al. | 600/109 |
| 7,474,327 B2 * | 1/2009 | Davidson et al. | 348/77 |
| 8,502,861 B2 * | 8/2013 | Hirakawa | 348/45 |
| 2002/0177779 A1 * | 11/2002 | Adler et al. | 600/476 |
| 2004/0027500 A1 | 2/2004 | Davidson et al. | |
| 2004/0206913 A1 * | 10/2004 | Costa et al. | 250/458.1 |
| 2005/0196017 A1 * | 9/2005 | Altherr et al. | 382/103 |
| 2006/0262966 A1 | 11/2006 | Eck et al. | |
| 2008/0089564 A1 * | 4/2008 | Sato et al. | 382/124 |

FOREIGN PATENT DOCUMENTS

| | | |
|---|---|---|
| JP | 2003-159220 | 6/2003 |
| JP | 2004-521662 | 7/2004 |
| JP | 2004-321603 | 11/2004 |
| JP | 2005-13573 | 1/2005 |
| JP | 2005-124965 | 5/2005 |
| JP | 2005-518160 | 6/2005 |
| WO | WO 03/069913 A1 | 8/2003 |

OTHER PUBLICATIONS

Decision of a Patent Grant dated Nov. 4, 2009 with English translation.

U.S. Office Action dated Aug. 2, 2011 received in related U.S. Appl. No. 11/787,980.

U.S. Office Action dated Jan. 11, 2012 of related U.S. Appl. No. 11/787,980.

* cited by examiner

IMAGE DISPLAY APPARATUS

TECHNICAL FIELD

The present invention relates to an image display apparatus that sequentially displays a series of input images, and particularly to an image display apparatus that is suitable for displaying a series of intra-subject images captured by using a capsule endoscope.

BACKGROUND ART

Recently, a swallowable capsule endoscope has been proposed in a field of an endoscope. The capsule endoscope including an imaging function and a radio communication function is swallowed by a patient from a mouth for an observation of inside of various organs, and travels through inside digestive organs such as a stomach, a small intestine, or a large intestine by a peristaltic movement to capture an image of the inside of the digestive organs one by one, until the capsule endoscope is naturally excreted from a human body.

An image data captured inside a body by the capsule endoscope while the capsule endoscope travels inside the organs is transmitted one by one to the outside of the body by radio communication, and stored in a memory provided in a receiver outside the body, or displayed on a display provided in the receiver. A doctor, a nurse, and the like makes a diagnosis based on the image displayed on a display by using the image data stored in the memory, or based on the image displayed at the same time of reception, on the display provided on the receiver.

Since number of a series of images captured by the capsule endoscope is generally enormous, a great amount of time and efforts are required for the doctor, the nurse, and the like to observe the series of images for making a diagnosis. In response to the above circumstance, such a display device has been proposed that determines a level of similarity between two images and changes a display rate of the images based on the determination result, when an observation is performed by displaying the images based on the image data stored in the memory (see, for example, Patent document 1). The above display device is configured, by focusing on such a point that a number of similar images are sequentially captured when a travel speed of the capsule endoscope slows down, so that when the similarity between two images is low, the images are to be displayed at a slow-display rate, while when the similarity is high, the images are to be displayed at a high-display rate.

Patent Document 1: Japanese Patent Application Laid-Open No. 2004-521662

DISCLOSURE OF INVENTION

Problem to be Solved by the Invention

However, with the above image display apparatus, because the display rate is changed depending on the similarity between the two images, even when an image includes a bleeding site and for which an observation is highly required, if the bleeding site is a tiny area, the similarity is determined as high and the image is displayed at the high-display rate. In this case, such a problem occurs that performing the observation becomes difficult.

The present invention is made in view of the above problems and an object of the present invention is to provide an image display apparatus that realizes to easily perform an observation of the images for which the observation is highly required, and to reduce a display time of an image for which the observation is less required, thereby realizing to effectively perform the observation of a series of images.

Means for Solving Problem

An image display apparatus according to the invention sequentially displaying a series of input images, includes an image classification unit that classifies each of images included in the series of images into at least one image group, based on a correlation level among each of the images; a feature-image detector that detects a feature-image area including a predetermined feature from each of the images, and detects each of feature images including the detected feature-image area from the series of images; a representative-image extracting unit that extracts the feature image in each of the image groups classified by the image classification unit, as a representative image that represents each of the image groups; and an image display controller that performs a control of sequentially displaying the representative image extracted by the representative-image extracting unit.

In the image display apparatus according to the invention, the representative-image extracting unit extracts at least a first image that is temporally at a top of each of the image groups, as the representative image of each of the image groups.

The image display apparatus according to the invention further includes a feature-image selector that calculates a variation amount of a predetermined feature amount of the feature-image area generated between the temporally continuous feature images from among a plurality of the feature images detected by the feature-image detector, and selects a feature-representative image that represents a plurality of the feature images based on the calculated variation amount, wherein the feature-image detector calculates the predetermined feature amount of each of the detected feature-image areas, the feature-image selector calculates the variation amount based on the feature amount calculated by the feature-image detector, and the representative-image extracting unit extracts the feature-representative image as the representative image from among the feature images in each of the image groups.

In the image display apparatus according to the invention, the predetermined feature amount is a position of the feature-image area in the feature-image.

In the image display apparatus according to the invention, the image display controller performs a control of displaying a mark indicating the feature image in a neighborhood of the representative image, when the representative image of the feature image is displayed.

In the image display apparatus according to the invention, each of the images is a captured image of an inside of organs, and the predetermined feature is a feature that indicates a lesion of the inside of the organs.

In the image display apparatus according to the invention, the feature that indicates the lesion is at least one of a bleeding, a discoloration, and a shape anomaly.

In the image display apparatus according to the invention, the series of images is generated by using a capsule endoscope.

Effect of the Invention

The image display apparatus according to the present invention enables to easily observe an image for which the observation is highly required, and to reduce a display time of an image for which the observation is less required, even when a series of images is classified based on a similarity between the images. As a result, it becomes possible to effectively observe the series of images.

Figure 1:
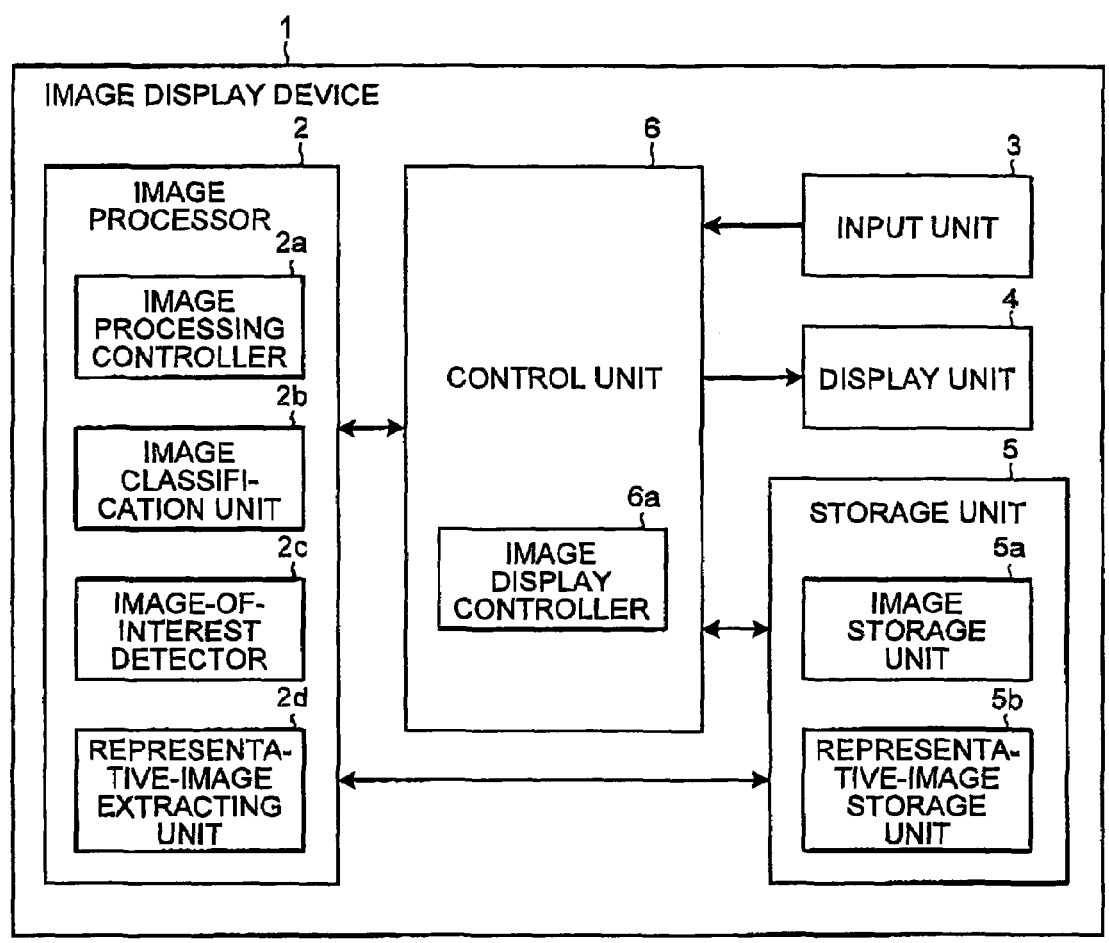
FIG. 1 is a block diagram of a configuration of an image display apparatus according to a first embodiment of the present invention.

EXPLANATIONS OF LETTERS OR NUMERALS 1, 11 age display apparatus
2, 12 Image processor
2a, 12a Image processing controller
2b Image classification unit
2c, 12c Image-of-interest detector
2d Representative-image extracting unit
12e Image-of-interest selector
3 Input unit
4 Display unit
5 Storage unit
5a Image storage unit
5b Representative-image storage unit
6 Control unit
6a Image display controller

BEST MODE(S) FOR CARRYING OUT THE INVENTION

Exemplary embodiments of an image display apparatus according to the present invention will be described in detail with reference to the accompanying drawings. The present invention is not limited to the below embodiments. For a description of the drawings, same reference numerals are assigned to same components.

First Embodiment

An image display apparatus according to a first embodiment of the present invention is described. FIG. 1 is a block diagram of a configuration of an image display apparatus 1 according to the present embodiment. As shown in FIG. 1, the image display apparatus 1 includes an image processor 2 that processes an image stored in a storage unit 5, an input unit 3 that accepts an input of various information, a display unit 4 that displays the various information, the storage unit 5 that stores the various information, and a control unit 6 that controls processes and operations for each of the units in the image display apparatus 1. The image processor 2, the input unit 3, the display unit 4, and the storage unit 5 are electrically connected to the control unit 6.

The image processor 2 includes an image processing controller 2a, an image classification unit 2b, an image-of-interest detector 2c, and a representative-image extracting unit 2d. The image processing controller 2a acquires an image from the storage unit 5, controls various image processes for the acquired image, and outputs and stores an image of the processing result in the storage unit 5. Specifically, the image processing controller 2a controls the image classification unit 2b, the image-of-interest detector 2c, and the representative-image extracting unit 2d to execute a predetermined image process.

The image classification unit 2b calculates a correlation value between two temporally continuous images acquired by the image processing controller 2a, associates a process-target-image with an existing image group or a new image group based on the calculated correlation value, and classifies a series of images into more than one group by repeating an association process to all sequential images.

More specifically, the image classification unit 2b refers to a threshold value corresponding to a previously input correlation value, associates the process-target-image with the existing image group or the new image group based on a value-size relationship between the threshold value and the calculated correlation value, and adds a group number corresponding to the associated image group to the process-target-image. The image classification unit 2b calculates, for example, a zero-mean normalized cross-correlation as the correlation value between each of pixel values corresponding to each of two images. It is acceptable that the image classification unit 2b obtains, for example, a color difference or a luminance difference corresponding to each of the pixels, as the correlation value, based on each of the pixel values.

The image-of-interest detector 2c as a feature-image detector detects a feature-image area that includes a predetermined feature from the images acquired by the image processing controller 2a, and detects a feature image that includes the detected feature-image area, as an image-of-interest that is to be paid attention to when an observation is performed. The image-of-interest detector 2c repeats the above detection process to all the sequential images to detect all the feature images as the images-of-interest. At this time, the image-of-interest detector 2c adds image-of-interest information indicating that an image is the image-of-interest to each of all the detected images.

The image-of-interest detector 2c detects the feature-image area by, for example, identifying a predetermined feature based on color information indicated by each of the pixels included in the image. It is acceptable that the image-of-interest detector 2c detects the feature-image area based not only on the color information but also on various feature amount such as an outline shape, texture, or concentration gradient.

The representative-image extracting unit 2d extracts a representative image that represents each of the image groups, from each of the image groups classified by the image classification unit 2b. More specifically, the representative-image extracting unit 2d extracts the images-of-interest in each of the image groups as the representative images for each of the image groups and extracts a first image that is temporally at the top in each of the image groups as the representative image. The representative-image extracting unit 2d sets a slow-display rate for displaying an image at a slow speed for the representative image that is the image-of-interest so that an adequate observation time is to be provided. On the other hand, the representative-image extracting unit 2d sets a normal-display rate for displaying an image at a normal speed that is faster than the slow-display rate for the representative image that is the first image.

The representative-image extracting unit 2d extracts all the images-of-interest with respect to each image group, and when the image-of-interest is not included in an image group, the representative-image extracting unit 2d exclusively extracts the first image. It is acceptable that the representative-image extracting unit 2d extracts a specific image in a predetermined order, such as an image temporally at the end in the image group, as the representative image instead of extracting the first image as the representative image.

Each of the representative images extracted by the representative-image extracting unit 2d is output to the storage unit 5 by the image processing controller 2a and stored in a representative-image storage unit 5b that is a storage area for storing the representative image. At this time, it is acceptable that the image processing controller 2a newly and exclusively stores a group number, image-of-interest information, and a display rate corresponding to each of the representative images by associating them with the original images, instead of storing each of the representative images.

The input unit 3 accepts an input of, for example, an image to be processed by the image display apparatus 1 and various process information. Specifically, the input unit 3 includes a communication interface such as a universal serial bus (USB) or an Institute of Electrical and Electronics Engineers (IEEE) 1394, and accepts an input of an image from an external device. The input unit 3 further includes various switches, an input key, a mouse, and a touch panel, and accepts an input of various types of the process information such as a threshold value to be referred to by the image classification unit 2b and information on a feature of the feature-image area to be detected by the image-of-interest detector 2c. It is acceptable that the input unit 3 includes an interface suitable for a portable recording medium such as various memory cards, a compact disc (CD), or a digital versatile disc (DVD) and accepts an input of an image from the portable recording medium.

The display unit 4 includes, for example, a liquid crystal display, and displays various information including the image. Specifically, the display unit 4 displays the image stored in the storage unit 5 and a graphical user interface (GUI) screen for requesting an operator of the image display apparatus 1 to input various process information.

The storage unit 5 is realized by a read only memory (ROM) in which various process programs are stored in advance, and a random access memory (RAM) that stores, for example, process parameters or process data for each of processes. Specifically, the storage unit 5 includes an image storage unit 5a that is a storage area for storing an image input from outside, and the representative-image storage unit 5b that is a storage area for storing the representative image extracted by the representative-image extracting unit 2d. It is acceptable that the storage unit 5 includes the portable recording medium such as various memory cards, a CD, and a DVD as a removable image storage unit.

The control unit 6 is realized by, for example, a central processing unit (CPU) that executes the various process programs stored in the storage unit 5. Specifically, the control unit 6 includes an image display controller 6a that performs a control of sequentially displaying a series of representative images stored in the representative-image storage unit 5b, on the display unit 4, based on the display rate set for each of the representative images. Further, when displaying the representative image that is the image-of-interest, the image display controller 6a performs a control of displaying an image-of-interest mark indicating that the image is the image-of-interest, in a neighboring area of the representative image. The image-of-interest mark is stored in advance in the storage unit 5, and if the image-of-interest information has been added to the process-target representative image, the image display controller 6a acquires the image-of-interest mark from the storage unit 5 and displays the image-of-interest mark with the image.

Figure 2:
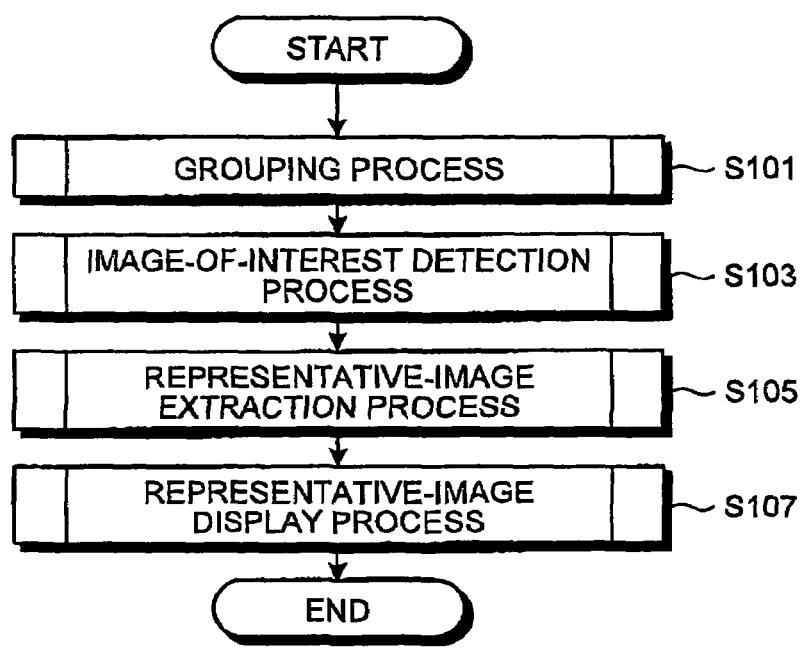
FIG. 2 is a flowchart of a process procedure performed by the image display apparatus shown in FIG. 1.

A process and an operation performed by the image display apparatus 1 are described. FIG. 2 is a flowchart of a process procedure of processing and displaying the series of images stored in the image storage unit 5a, performed by the image display apparatus 1 under a control of the control unit 6. The flowchart shown in FIG. 2 describes an example of the process procedure of displaying the series of images generated by capturing images of inside of organs such as a digestive organ by using a not shown capsule endoscope.

As shown in FIG. 2, the image classification unit 2b performs a grouping process for classifying each of the images included in the series of images stored in the image storage unit 5a into each of the image groups (step S101). The image-of-interest detector 2c performs an image-of-interest detection process for detecting the image-of-interest from the series of images (step S103). The representative-image extracting unit 2d performs a representative-image extraction process for extracting the image-of-interest and the first image in each of the classified image groups, as the representative image (step S105). The image display controller 6a performs a representative-image display process for sequentially displaying the extracted series of representative images, based on the display rate set for each of the representative images (step S107). The control unit 6 terminates a series of processes.

Figure 3:
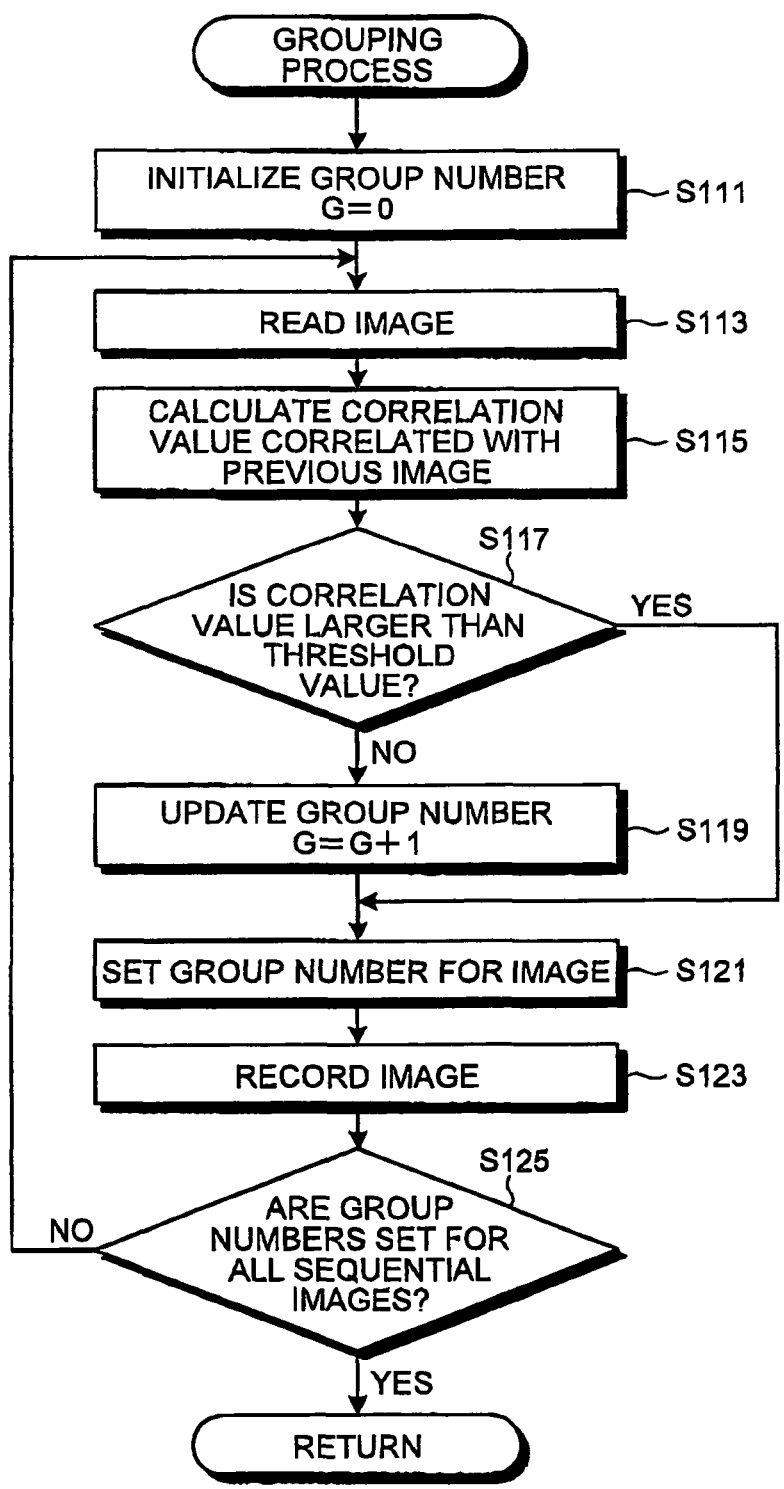
FIG. 3 is a flowchart of a process procedure of a grouping process shown in FIG. 2.

Next, the grouping process at step S101 shown in FIG. 2 is described. FIG. 3 is a flowchart of a process procedure of the grouping process. As shown in FIG. 3, the image processing controller 2a initializes a parameter G, which represents the group number corresponding to the image group, as G=0 (step S111), and reads two images temporally at the top and in a second order, from the series of images stored in the image storage unit 5a (step S113).

The image classification unit 2b determines an image in temporally second order as the process-target-image and calculates the correlation value correlated with a previous image that is the first image obtained at a previous time point (step S115), and determines whether the calculated correlation value is larger than the previously input threshold value (step S117). When the correlation value is smaller than the threshold value (step S117: No), the image classification unit 2b determines that a similarity between the images is low and updates the group number by incrementing the parameter G (step S119). The image classification unit 2b sets the updated group number for the process-target-image (step S121). On the other hand, when the correlation value is larger than the threshold value (step S117: Yes), the image classification unit 2b determines that the similarity between the images is high and sets the group number represented by the current parameter G for the process-target-image (step S121). The image classification unit 2b sets a group number of "0" to the first image.

Thereafter, the image processing controller 2a records the image for which the group number is set in the image storage unit 5a (step S123), and determines whether the group numbers are set for all the images included in the series of images (step S125). When the group numbers are not set for all the images (step S125: No), the image processing controller 2a performs a control of repeating the processes from step S113 to the images for which the group numbers are not set. On the other hand, when the group numbers are set for all the images (step S125: Yes), the image processing controller 2a returns the process to step S101.

As described, with the grouping process at step S101, the image having a high similarity with the previous image is associated with the same image group as that of the previous image, while the image having a low similarity with the previous image is associated with a new image group of which group number is updated. Accordingly, the series of images is classified so that a single image group includes the images that have the similarities.

Figure 4:
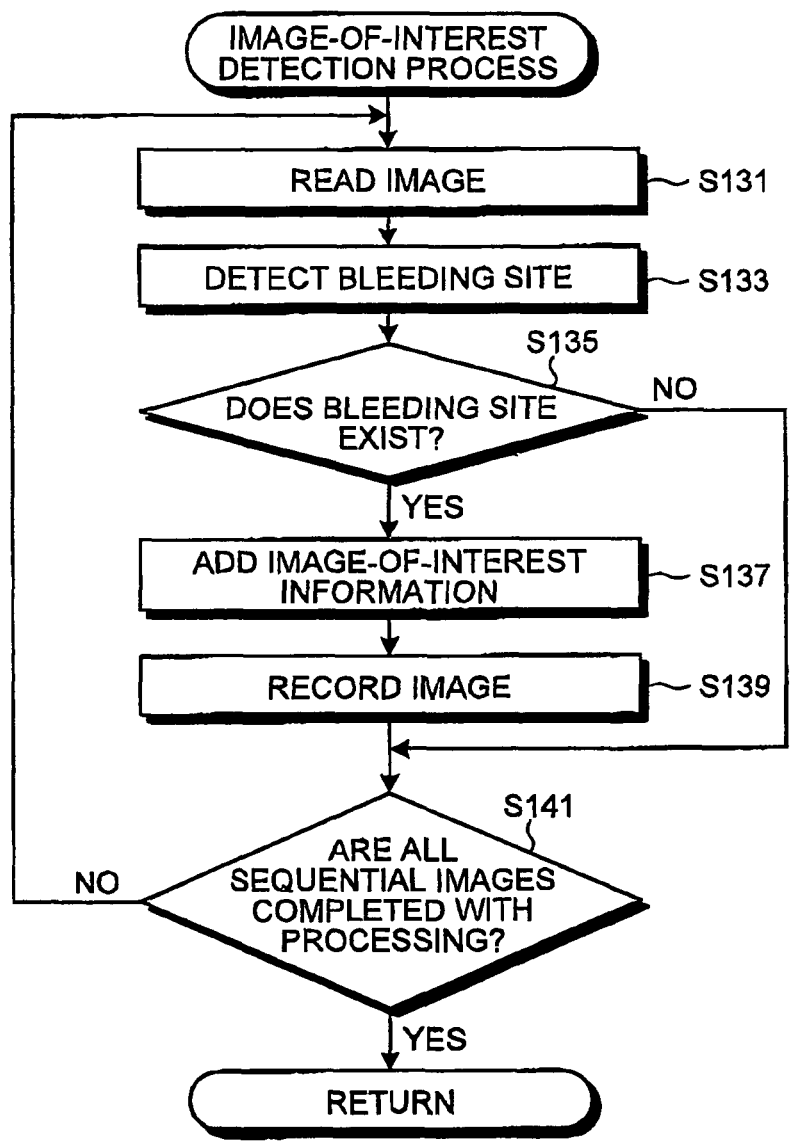
FIG. 4 is a flowchart of a process procedure of an image-of-interest detection process shown in FIG. 2.

Next, the image-of-interest detection process at step S103 shown in FIG. 2 is described. FIG. 4 is a flowchart of a process procedure of the image-of-interest detection process. As shown in FIG. 4, the image processing controller 2a reads the temporally first image from the series of images for which the group number is set and which is stored in the image storage unit 5a (step S131). The image-of-interest detector 2c detects an image area that represents a bleeding site as the feature-image area from the read images (step S133) and determines whether the detected bleeding site exists (step S135). It is preferable that, the image-of-interest detector 2c detects an image area having darker red than a mucous membrane of inside of organs, as the bleeding site, when detecting the bleeding site.

When the detected bleeding site exists (step S135: Yes), the image-of-interest detector 2c adds the image-of-interest information to the process-target-image (step S137). The image processing controller 2a records the image with the image-of-interest information added in the image storage unit 5a (step S139) and determines whether all the sequential images are completed with processing (step S141).

When all the images are not completed with processing (step S141: No), the image processing controller 2a repeats the processes from step S131 to the images that are not completed with processing. When all the images are completed with processing (step S141: Yes), the process returns to step S103. When it is determined that the detected bleeding site does not exist at step S135 (step 135: No), the image processing controller 2a immediately performs a determination at step S141.

As described, with the image-of-interest detection process at step S103, it is possible to detect the image of the bleeding site captured inside the organs, as the image-of-interest, from the series of images. The image to be detected as the image-of-interest is not limited to the captured image of the bleeding site, and other captured images of various sites of suspected lesion, for example, a discoloration site of the inside of organs and a shape anomaly site, can be detected as the image-of-interest. In this case, it is preferable that the image-of-interest detector 2c detects an image area representing a feature of, for example, the discoloration and the shape anomaly, as the feature-image area.

Figure 5:
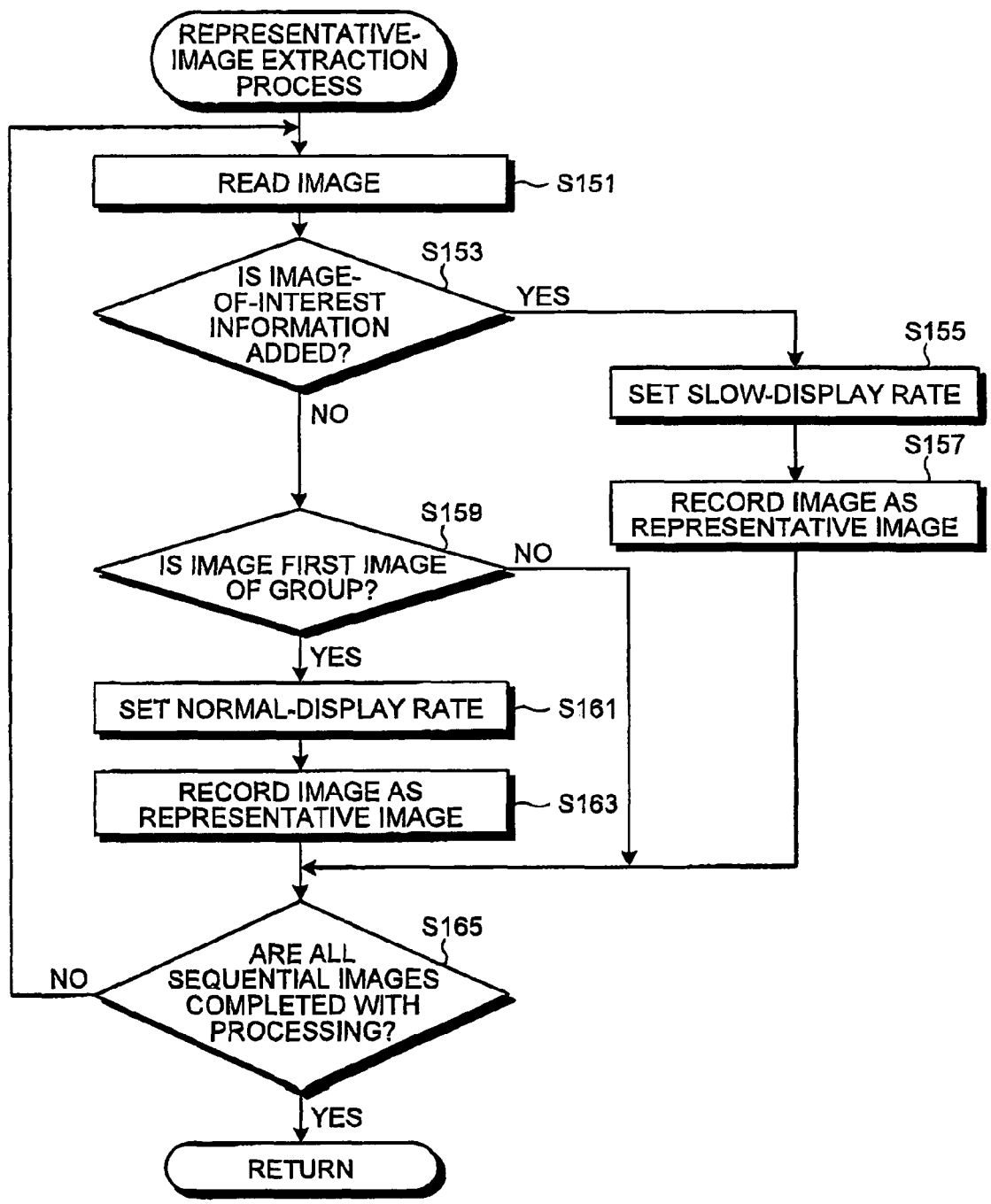
FIG. 5 is a flowchart of a process procedure of a representative-image extraction process shown in FIG. 2.

Next, the representative-image extraction process at step S105 shown in FIG. 2 is described. FIG. 5 is a flowchart of a process procedure of the representative-image extraction process. As shown in FIG. 5, the image processing controller 2a reads the temporally first image from the series of images, for which the grouping process and the image-of-interest detection process have been performed and which is stored in the image storage unit 5a (step S151). The representative-image extracting unit 2d determines whether the image-of-interest information is added to the read image (step S153).

When the image-of-interest information is added (step S153: Yes), the representative-image extracting unit 2d sets the slow-display rate to the process-target-image (step S155), and the image processing controller 2a records the image-of-interest with the set slow-display rate in the representative-image storage unit 5b, as the representative image (step S157).

On the other hand, when the image-of-interest information is not added (step S153: No), the representative-image extracting unit 2d determines whether the process-target-image is the first image of the image group (step S159). When the process-target-image is the first image (step S159: Yes), the representative-image extracting unit 2d sets the normal-display rate for the process-target-image (step S161), and the image processing controller 2a records the first image with the set normal-display rate in the representative-image storage unit 5b, as the representative image (step S163).

After the step S157 or step S163 is performed, the image processing controller 2a determines whether all the sequential images are completed with processing (step S165). When all the images are not completed with processing (step S165: No), the image processing controller 2a repeats the processes from S151 to all the images with which the processing is not completed. When all the images are completed with processing (step S165: Yes), the process returns to step S105. When it is determined that the process-target-image is not the first image at step S159 (step S159: No), the image processing controller 2a immediately performs a determination at step S165.

Figure 6:
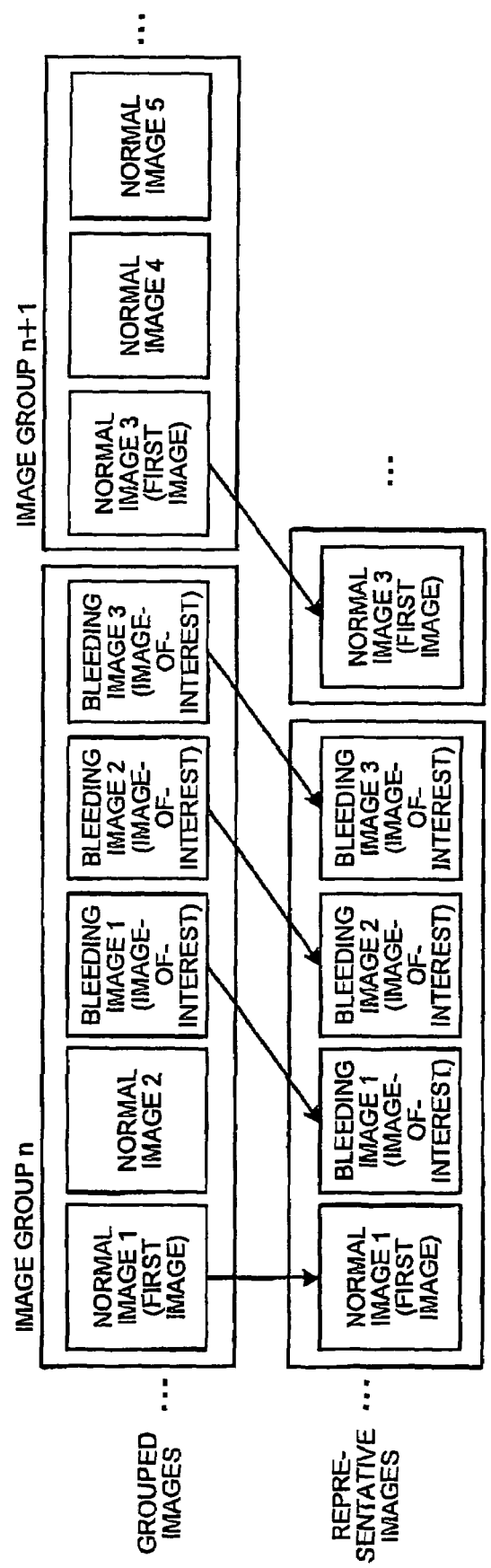
FIG. 6 is a schematic view for describing an example of a result of the representative-image extraction process shown in FIG. 5.

As described, with the representative-image extraction process at step S105, as shown in FIG. 6, the first image and the image-of-interest in each of the image groups can be extracted as the representative images. In an example shown in FIG. 6, a "normal image 1" that is the first image and a "bleeding image 1" to a "bleeding image 3" that are the images-of-interest are extracted as the representative images from an image group n that is the image group in nth order in time series, while a "normal image 3" that is the first image is extracted as the representative image from an image group n+1. The extracted series of representative images is stored in time series in the representative-image storage unit 5b.

Figure 7:
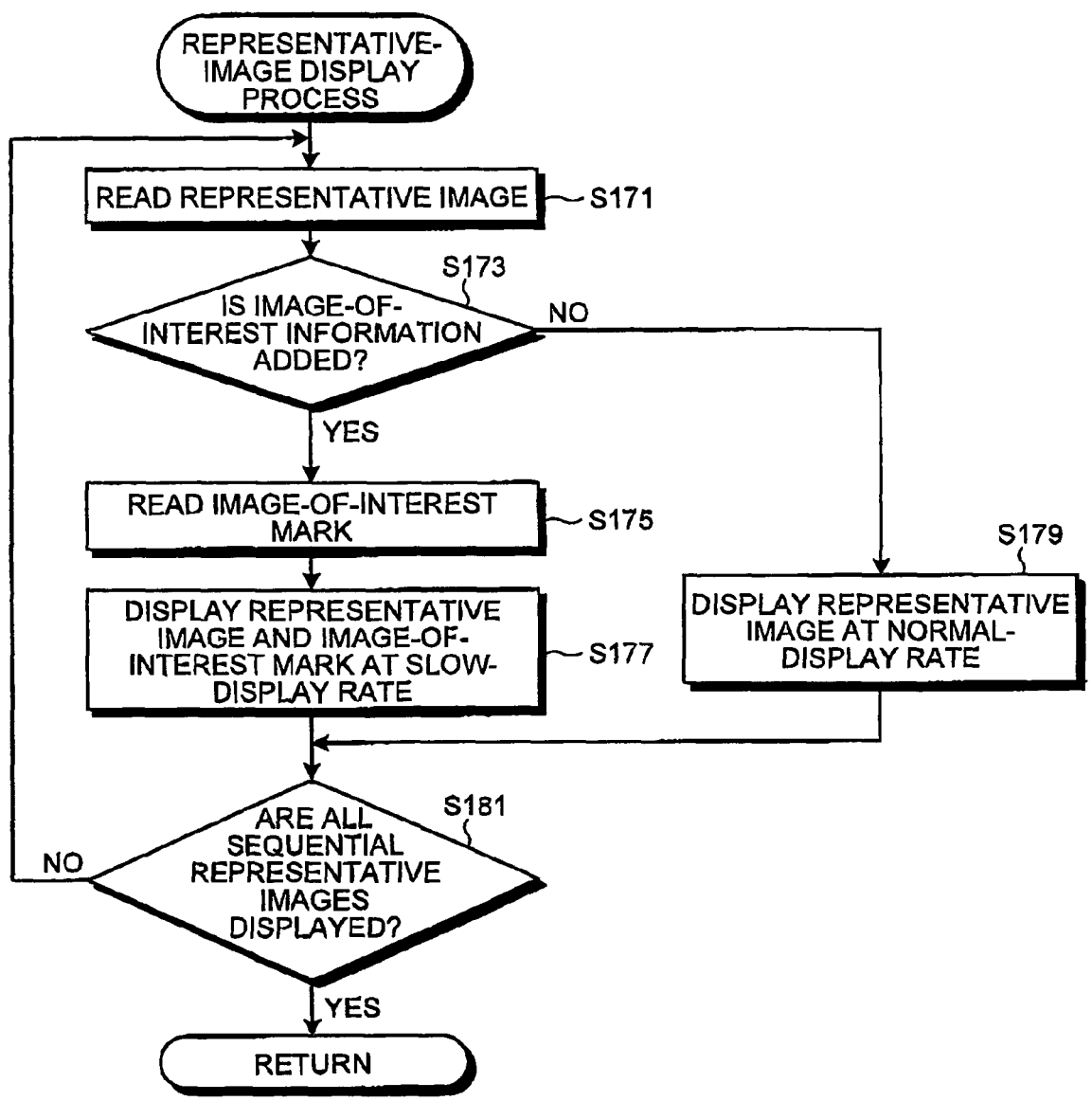
FIG. 7 is a flowchart of a process procedure of a representative-image display process shown in FIG. 2.

Next, the representative-image display process at step S107 shown in FIG. 2 is described. FIG. 7 is a flowchart of a process procedure of the representative-image display process. As shown in FIG. 7, the image display controller 6a reads the temporally first image from the series of representative images stored in the representative-image storage unit 5b (step S171), and determines whether the image-of-interest information is added (step S173).

Then the image-of-interest information is added (step S173: Yes), the image display controller 6a reads the image-of-interest mark from the storage unit 5 (step S175), and displays the read representative image and the image-of-interest mark on the display unit 4 at the slow-display rate (step S177). Accordingly, the image display controller 6a makes it possible to display the representative image of the image-of-interest for which the observation is highly required for a longer time than a normal time. On the other hand, when the image-of-interest information is not added (step S173: No), the image display controller 6a displays the read representative image on the display unit 4 at the normal-display rate (step S179).

Thereafter, the image display controller 6a determines whether all the sequential representative images are displayed (step S181). When all the representative images are not displayed (step S181: No), the image display controller 6a repeats the processes from step S171 to the not displayed representative images. When all the representative images are displayed (step S181: Yes), the process returns to step S107. As described, the image display controller 6a sequentially displays the series of representative images stored in the representative-image storage unit 5b, based on each of the display rates set for each of the images.

Figure 8:
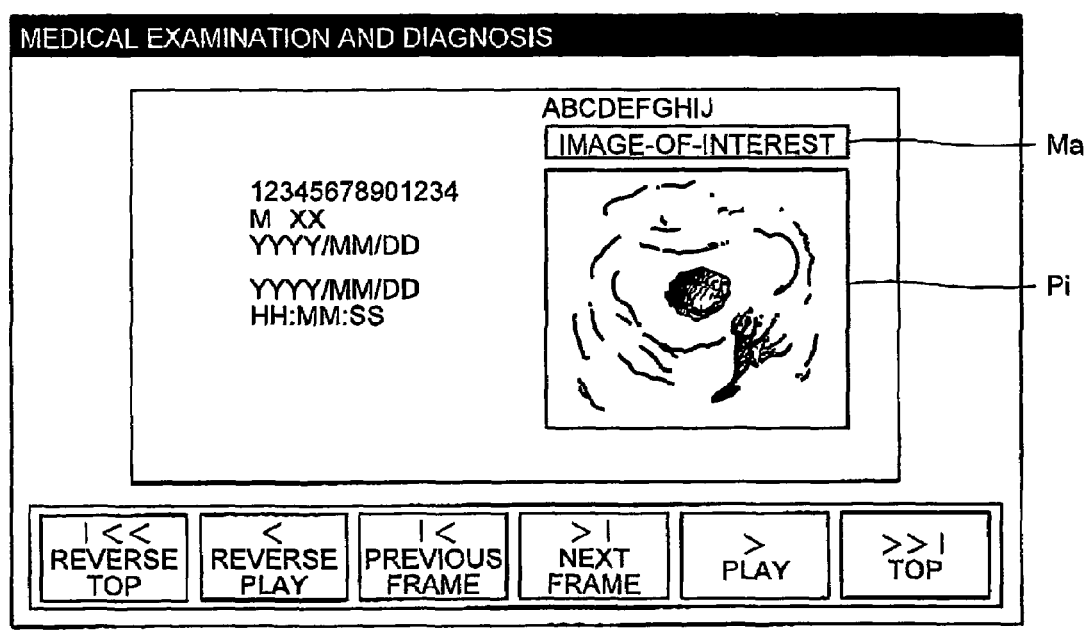
FIG. 8 is a schematic view of an example of a graphic user interface (GUI) screen displayed by the image display apparatus shown in FIG. 1.

FIG. 8 is a schematic view of an example of a graphic user interface (GUI) screen displayed on the display unit 4 when the representative image is displayed. With an example shown in FIG. 8, in a "medical examination/diagnosis" window, a representative image Pi of the image-of-interest, an image-of-interest mark Ma, and text information that represents various attributes of the representative image Pi are displayed.

As described above, with the image display apparatus 1 according to the first embodiment, the image classification unit 2b calculates the correlation value between the temporally continuous images in the series of images stored in the image storage unit 5a, and classifies the series of images based on the calculated correlation value. The image-of-interest detector 2c detects the feature-image area from each of the images and detects the feature image that includes the detected feature-image area, as the image-of-interest. The representative-image extracting unit 2d extracts the image-of-interest and the first image in each of the image groups as the representative images and sets the display rate for each of the extracted representative images. The image display controller 6a sequentially displays the series of representative images based on the set display rates. Accordingly, it becomes possible to easily observe the images that include, for example, the bleeding site and for which the observation is highly required. Further, it becomes possible to reduce a display time by exclusively displaying the first image of each of the image groups instead of displaying the images that do not include the bleeding sites and for which the observations are less required. As a result, it becomes possible to effectively observe the series of images.

Second Embodiment

Next, a second embodiment of the present invention will be described. According to the first embodiment described above, it is configured so that all the images-of-interest detected by the image-of-interest detector 2c are displayed as the representative images. Alternately, according to the second embodiment, when a plurality of the images-of-interest shows the same features, one representative image is selected from among the images-of-interest for a display.

Figure 9:
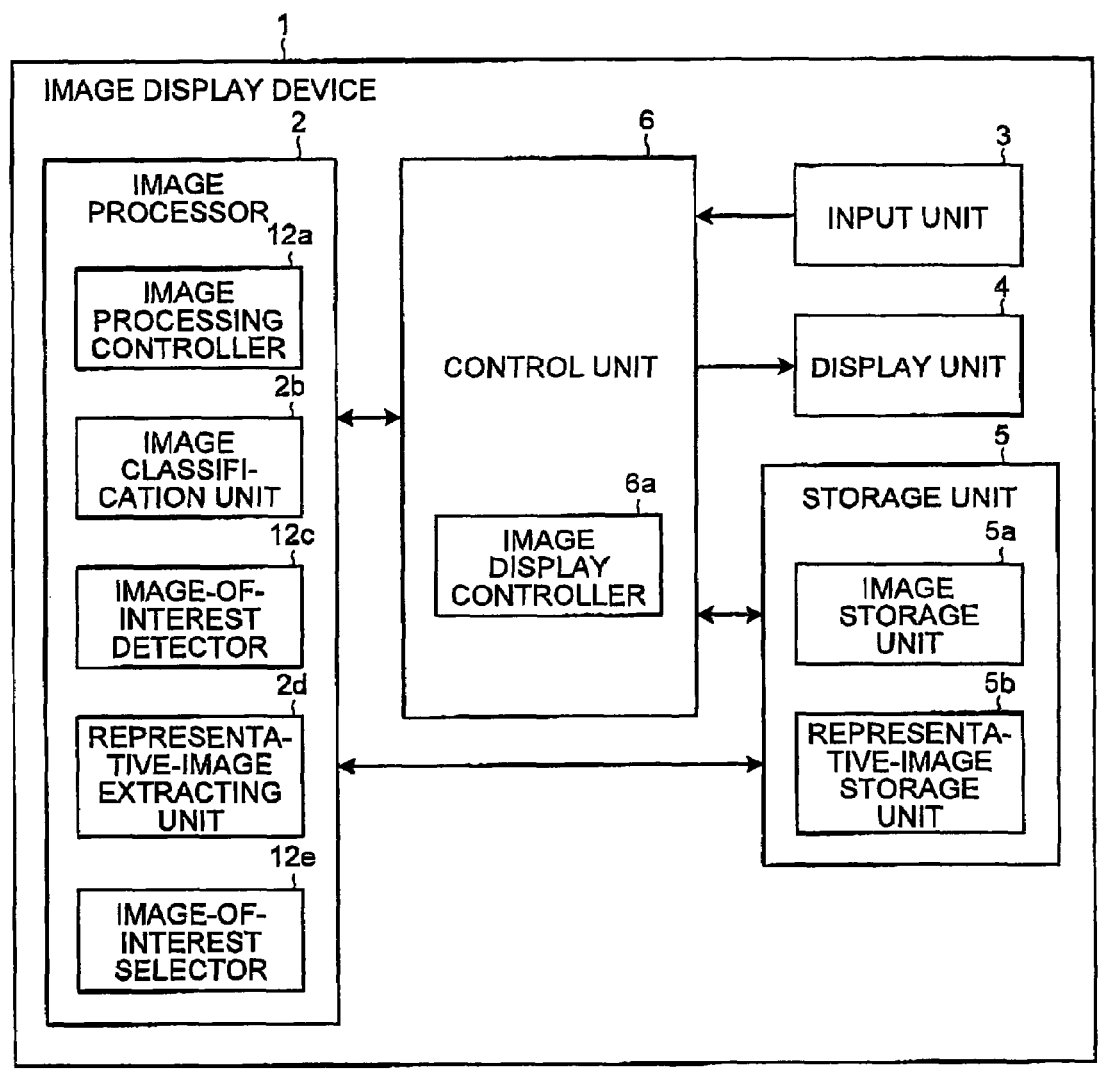
FIG. 9 is a block diagram of a configuration of an image display apparatus according to a second embodiment of the present invention.

FIG. 9 is a block diagram of a configuration of an image display apparatus 11 according to the second embodiment. As shown in FIG. 9, the image display apparatus 11 includes an image processor 12 instead of the image processor 2 included in the image display apparatus 1. The image processor 12 includes an image processing controller 12a and an image-of-interest detector 12c instead of the image processing controller 2a and the image-of-interest detector 2c included in the image display apparatus 1, and further includes an image-of-interest selector 12e. Other configurations are the same as those in the first embodiment and the same reference numerals are assigned to the same components.

The image processing controller 12a, similar to the image processing controller 2a, acquires an image stored in the storage unit 5, process the image, and stores the image of the processing result in the storage unit 5. In this case, the image processing controller 12a controls the image-of-interest detector 12c instead of the image-of-interest detector 2c and further controls the image-of-interest selector 12e to select a representative image-of-interest as the representative image, from among a plurality of images-of-interest that shown the same features.

The image-of-interest detector 12c, similar to the image-of-interest detector 2c, detects the image-of-interest from the series of images, calculates the feature amount of the feature-image area of each of the detected images-of-interest, and associates information indicating the calculated feature amount with the images-of-interest. More specifically, the image-of-interest detector 12c calculates, as the feature amount, a position of the feature-image area in the image-of-interest, generates position information that indicates the calculated position, and adds the generated position information to the image-of-interest. The position of the feature-image area is indicated by at least one of, for example, a position of center of gravity of the feature-image area, maximum or minimum position of the luminance, a position having a predetermined color, and a most peripheral position of the feature-image area.

The image-of-interest selector 12e selects the representative image-of-interest that represents the images-of-interest, from among the images-of-interest detected by the image-of-interest detector 12c, based on a position change of the feature-image area generated between the temporally continuous images-of-interest. More specifically, the image-of-interest selector 12e calculates a motion vector that indicates the position change of the feature-image area generated between the two continuous images-of-interest and determines whether the two feature-image areas are the image areas that show the same features, based on the calculated motion vector. When the image areas show the same features, the image-of-interest selector 12e changes a status of one image-of-interest to a cancelled image-of-interest that is not to be extracted as the representative image. The image-of-interest selector 12e repeats the above process to the series of images-of-interest, resulting in selecting the image-of-interest that is not to be the cancelled image-of-interest, as the representative image-of-interest.

Figure 10:
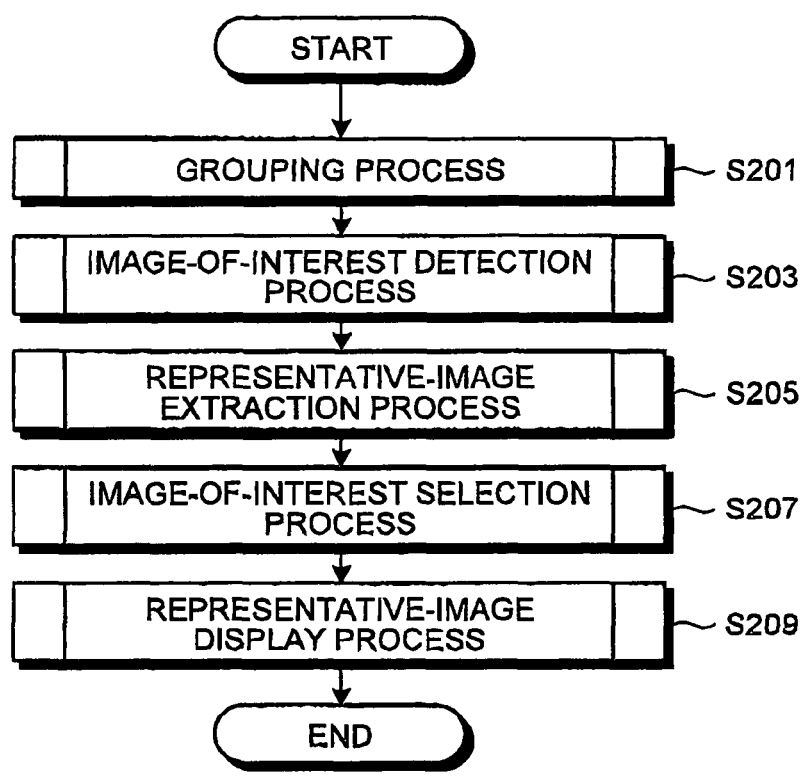
FIG. 10 is a flowchart of a process procedure performed by the image display apparatus shown in FIG. 9.

A process and an operation performed by the image display apparatus 11 is described. FIG. 10 is a flowchart of a process procedure of processing and displaying the series of images stored in the image storage unit 5a performed by the image display apparatus 11, under a control of the control unit 6. The flowchart shown in FIG. 10 is an example of the process procedure of displaying the series of images generated by capturing images of the inside of the organs such as a digestive organ, by using a not shown capsule endoscope.

As shown in FIG. 10, the image classification unit 2b performs the grouping process similar to step S101 (step S201). The image-of-interest detector 12c performs the image-of-interest detection process for detecting the image-of-interest from the series of images (step S203). The image-of-interest selector 12e performs the image-of-interest selection process for selecting the representative image-of-interest from the images-of-interest detected at step S203 (step S205). The representative-image extracting unit 2d performs the representative-image extraction process similar to step S105 (step S207). The image display controller 6a performs the representative-image display process similar to step S107 (step S209). The control unit 6 terminates a series of processes.

The process procedures for the grouping process at step S201, the representative-image extraction process at step S207, and the representative-image display process at step S209 are described with the flowcharts shown in FIG. 3, FIG. 5, and FIG. 7. The image-of-interest detection process at step S203 and the image-of-interest selection process at step S205 are described below.

Figure 11:
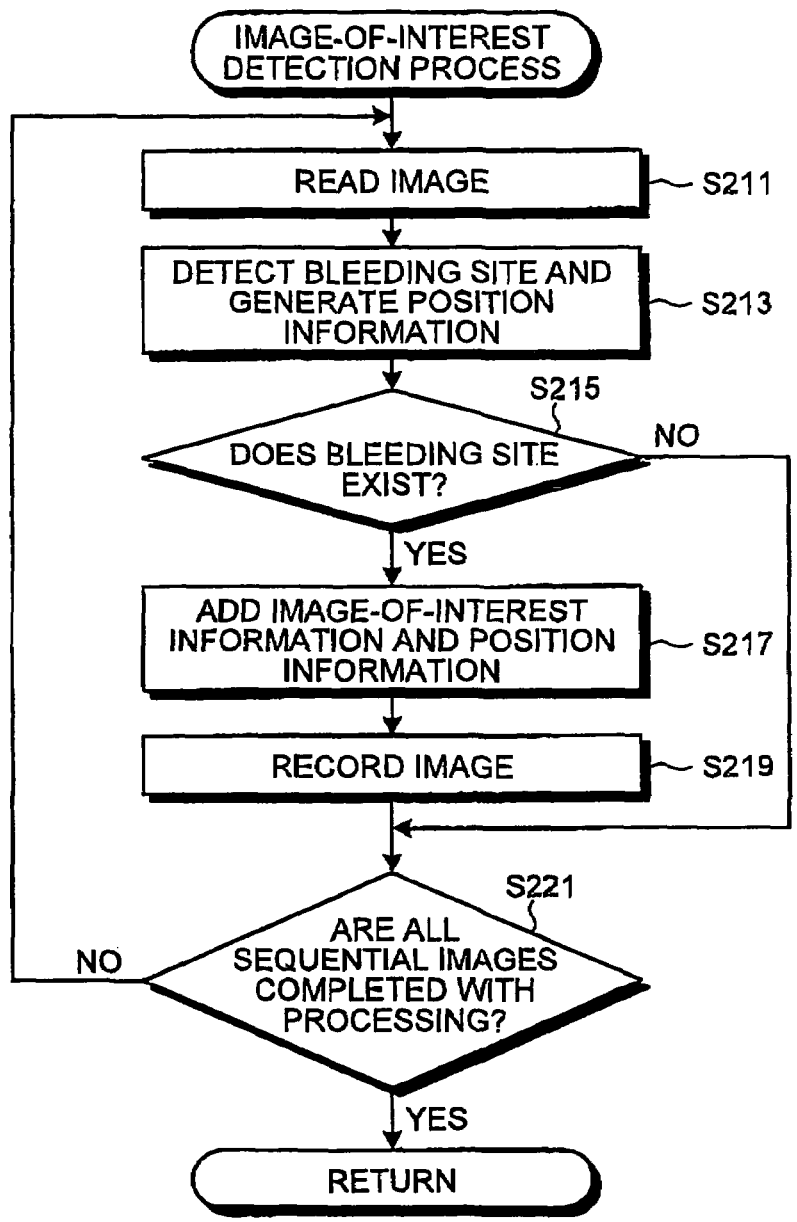
FIG. 11 is a flowchart of a process procedure of an image-of-interest detection process shown in FIG. 10.

FIG. 11 is a flowchart of a process procedure of the image-of-interest detection process at step S203. As shown in FIG. 11, the image processing controller 12a reads the temporally first image from the series of images, for which the group number is set and which is stored in the image storage unit 5a (step S211). The image-of-interest detector 12c detects an image area that represents the bleeding site as the feature-image area from the read images and generates the position information that indicates the position of the bleeding site (step S213).

The image-of-interest detector 12c determines whether the detected bleeding site exists (step S215). When the detected bleeding site exists (step S215: Yes), the image-of-interest detector 12c adds the image-of-interest information and the position information generated at step S213 to the process-target-image (step S217). The image processing controller 12a records the image with the image-of-interest information and the position information added in the image storage unit 5a (step S219), and determines whether all the sequential images are completed with processing (step S221).

When all the sequential images are not completed with processing (step S221: No), the image processing controller 12a repeats the processes from step S211 to the images with which the processing is not completed. When all the sequential images are completed with processing (step S221: Yes), the process returns to step S203. When it is determined that the detected bleeding site does not exist at step S215 (step S215: No), the image processing controller 12a immediately performs a determination at step S221.

As described, with the image-of-interest detection process at step S203, it becomes possible to detect the image of the bleeding site captured inside the organs from the series of images and to add the position information that indicates the position of the bleeding site to the detected image-of-interest. The image area detected as the feature-image area is not limited to the image area that represents the bleeding site, and can be other image areas that represent various features of suspected lesion, for example, the discoloration site and the shape anomaly site, of the inside of the organ.

Figure 12:
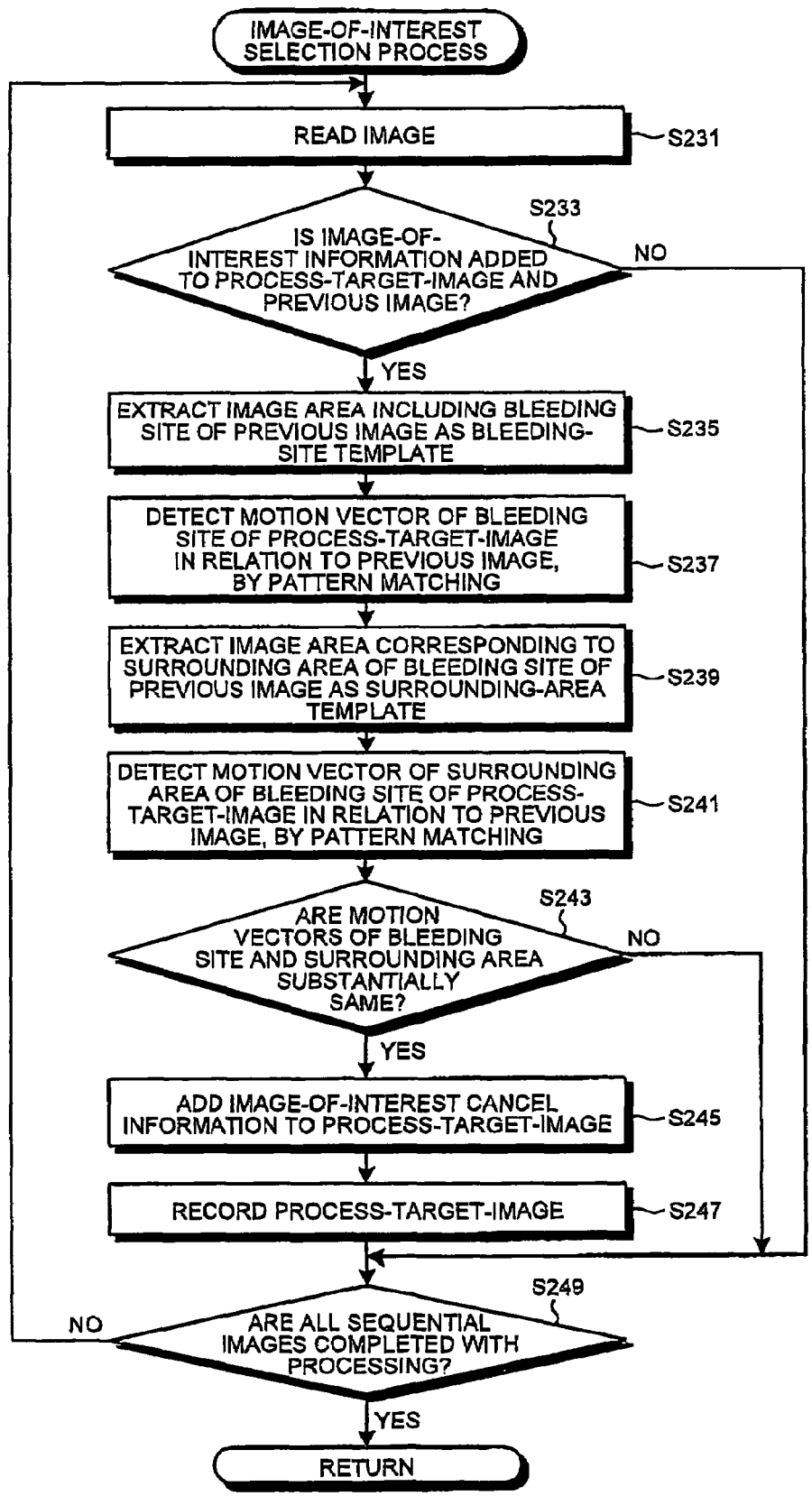
FIG. 12 is a flowchart of a process procedure of an image-of-interest selection process shown in FIG. 10.

Next, the image-of-interest selection process at step S205 shown in FIG. 10 is described. FIG. 12 is a flowchart of a process procedure of the image-of-interest selection process. As shown in FIG. 12, the image processing controller 12a reads two continuous images temporally at the top and in a second order from the series of images, for which the image-of-interest detection process is performed and which is stored in the image storage unit 5a (step S231). The image-of-interest selector 12e determines a temporally second image as the process-target-image and determines whether the image-of-interest information is added to a previous image that is the first image obtained at a previous time point, and to the process-target-image (step S233).

When the image-of-interest information is added to the process-target-image and the previous image (step S233: Yes), the image-of-interest selector 12e refers to the position information that indicates the position of the bleeding site, and extracts the image area including the bleeding site of the previous image as a bleeding-site template that is a template for a pattern matching process (step S235). The image-of-interest selector 12e performs the pattern matching for the process-target-image based on the bleeding-site template, detects the image area that represents the bleeding site highly correlated with the bleeding-site template, and detects a motion vector that indicates the position change of the bleeding site of the process-target-image in relation to the previous image (step S237).

Thereafter, the image-of-interest selector 12e extracts the image area in a surrounding area of the bleeding site, which has a predetermined position relation with the bleeding site, from the previous images, as the surrounding-area template (step S239). The image-of-interest selector 12e performs the pattern matching for the process-target-image based on the surrounding-area template, detects the image area highly correlated with the surrounding-area template, and detects the motion vector that indicates the motion of the surrounding area of the bleeding site of the process-target-image in relation to the previous image (step S241).

The image-of-interest selector 12e determines whether the detected motion vector of the bleeding site and the motion vector of the surrounding area of the bleeding site are substantially the same (step S243). When the motion vectors are substantially the same (step S243: Yes), the image-of-interest selector 12e adds the image-of-interest cancel information for indicating the cancelled image-of-interest to the process-target-image (step S245).

Thereafter, the image processing controller 12a records the process-target-image with the image-of-interest cancel information added in the image storage unit 5a (step S247), determines whether all the sequential images are completed with processing (step S249). When all the sequential images are not completed with processing (step S249: No), the image processing controller 12a repeats the processes from step S231 to the images with which the processing is not completed. When all the sequential images are completed with processing (step S249: Yes), the process returns to step S205.

When it is determined that the image-of-interest information is not added at step S233 (step S233: No), and when it is determined that each of the motion vectors is not the same at step S243 (step S243: No), the image processing controller 12a immediately performs a determination at step S249.

At step S237 and step S241, the image-of-interest selector 12e compares, on the same screen, each of the templates extracted from the previous image to the image area in the process-target-image associated by the pattern matching, to detect the motion vector that indicates the position change of the gravity of each of the image areas. At step S237, it is acceptable that the image-of-interest selector 12e obtains the motion vector from a position coordinate between the bleeding sites of the previous image and of the process-target-image, without performing the pattern matching.

At step S243, for the detected motion vectors of the bleeding site and the motion vector of the surrounding area of the bleeding site, the image-of-interest selector 12e determines whether each of the detected motion vectors is the same, based on whether differences between each of the vector azimuths and sizes for each of the motion vectors are larger than the predetermined threshold values. Further, it is acceptable that the image-of-interest selector 12e determines whether each of the motion vectors is the same, by calculating a vector difference between each of the motion vectors, an inner product, or an outer product, and by using at least one of the calculation results.

At step S245, when the motion vector of the bleeding site and the motion vector of the surrounding area of the bleeding site are the substantially the same, the image-of-interest selector 12e determines that there is a high possibility that the bleeding site of the process-target-image and the bleeding site of the previous image are the same, and a requirement for displaying the process-target-image is low when an observation is performed. Thereafter, the image-of-interest selector 12e adds the image-of-interest cancel information to the process-target-image. It is preferable that the image-of-interest selector 12e detects a plurality of the image areas as the surrounding-area template at step S239, so that the image-of-interest selector 12e can determine the identification of the bleeding site with high accuracy.

As described, with the image-of-interest selection process at step S205, by comparing the motion of the image areas of the bleeding site and the surrounding area of the bleeding site between the two continuous images-of-interest, it becomes possible to determine whether the bleeding sites of the two images-of-interest are the same. When the bleeding sites are the same, one image-of-interest can be changed to the cancelled image-of-interest. The process procedures of steps S235 to S241 can be changed if required. For example, the process procedures of steps between S237 and S239 can be replaced with each other.

Figure 13:
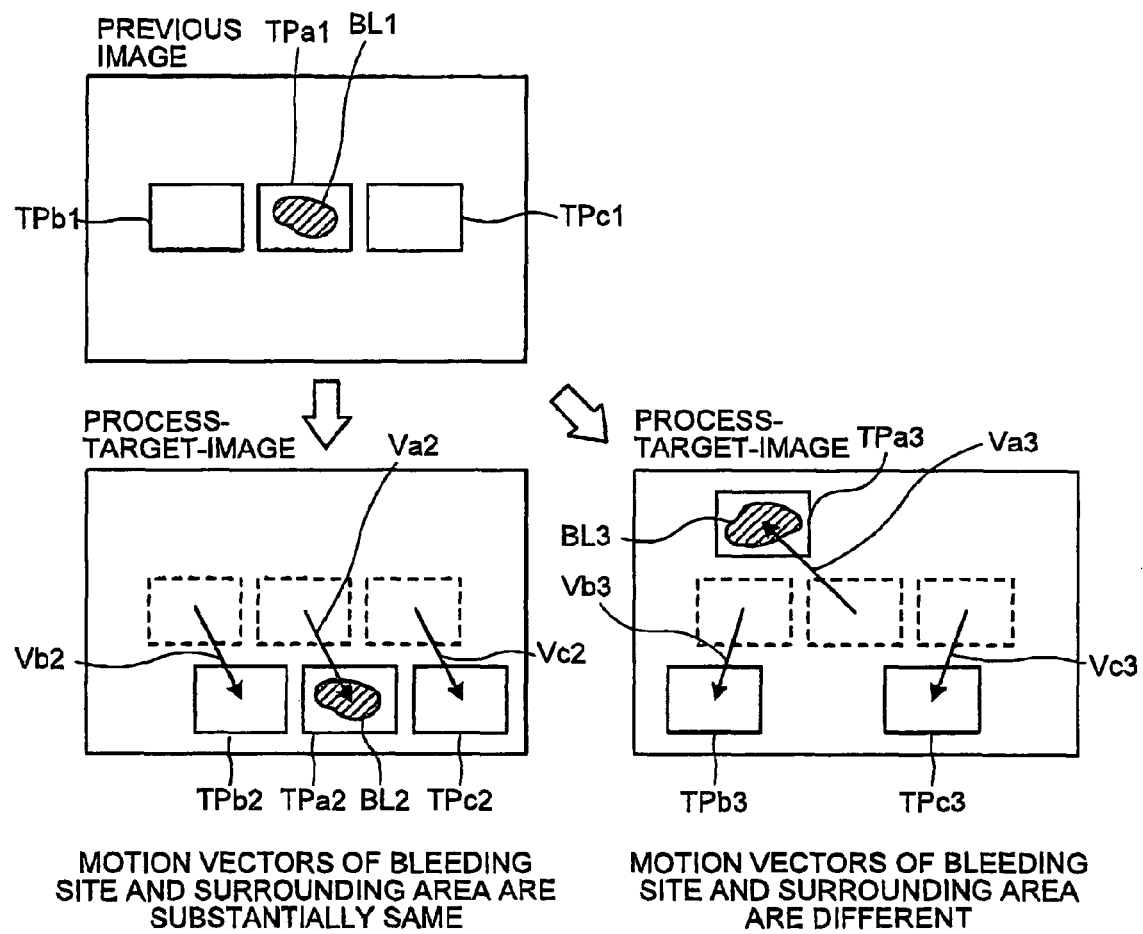
FIG. 13 is a schematic view for describing an example of the image-of-interest selection process shown in FIG. 12.

The image-of-interest selection process shown in FIG. 12 is described in detail. FIG. 13 is a schematic view for describing an example of an image to be processed in the image-of-interest selection process. As shown in FIG. 13, the image-of-interest selector 12e extracts an image area TPa1 including a bleeding site BL1 of the previous image as the bleeding-site template, and extracts an image area TPb1 positioned on a left side and an image area TPc1 positioned on a right side of the bleeding site BL1 in the drawings, as the surrounding-area template. Thereafter, the image-of-interest selector 12e performs the template matching for the process-target-image, based on the templates.

As a result of the template matching, when image areas TPa2, TPb2, and TPc2 of the process-target-image are detected in relation to each of the image areas TPa1, TPb1, and TPc1 of the previous image, the image-of-interest selector 12e detects motion vectors Va2, Vb2, and Vc2 that indicate a motion of the center 6f the gravity of each of the corresponding image areas. Thereafter, the image-of-interest selector 12e determines whether the vector azimuth and the size of each of the motion vectors are smaller than predetermined threshold values.

In the case of the motion vectors Va2, Vb2, and Vc2 shown in FIG. 13, the image-of-interest selector 12e determines that each of the motion vectors is substantially the same, determines that the bleeding site BL2 of the process-target-image is substantially the same with the bleeding site BL1, and adds the image-of-interest cancel information to the process-target-image.

On the other hand, as a result of the template matching, when the image areas TPa3, TPb3, and TPc3 of the process-target-image are detected, the image-of-interest selector 12e detects the motion vectors Va3, Vb3, and Vc3, and determines whether the vector azimuth and the size of each of the motion vectors are smaller than the predetermined threshold values.

In the case of the motion vectors Va3, Vb3, and Vc3 shown in FIG. 13, the image-of-interest selector 12e determines that each of the motion vectors is unique, determines that the bleeding site BL3 of the process-target-image is different from the bleeding site BL1, and selects the process-target-image as the representative image-of-interest.

Figure 14:
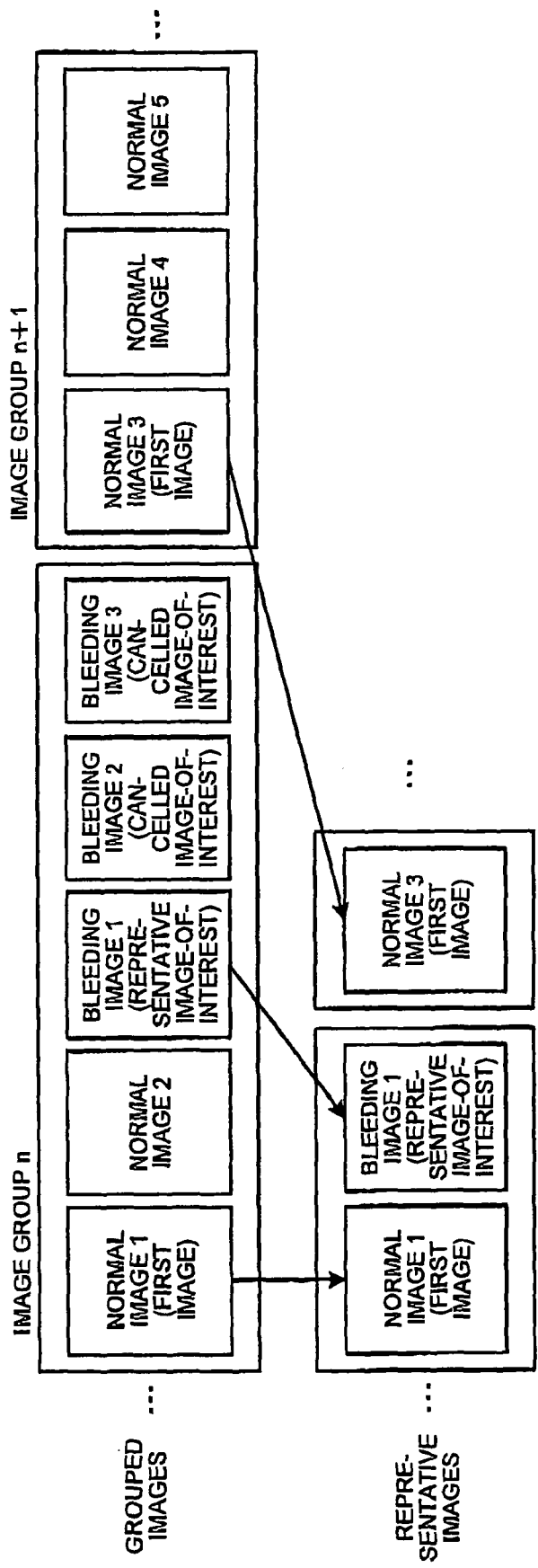
FIG. 14 is a schematic view for describing an example of a result of the image-of-interest selection process shown in FIG. 12.

As a result of performing the image-of-interest selection process, with the representative-image extraction process at step S207, as shown in FIG. 14, the first image and the representative image-of-interest are extracted as the representative images from each of the image groups. In an example shown in FIG. 14, a "normal image 1" that is the first image and a "bleeding image 1" that is the representative image-of-interest are extracted as the representative images from an image group n that is the image group in nth order in time series, while a "normal image 3" that is the first image is detected as the representative image from an image group n+1. The extracted series of representative images are stored in time series in the representative-image storage unit 5b.

As described above, with the image display apparatus 11 according to the second embodiment, the image-of-interest detector 12c detects the image-of-interest from the series of images classified into an image group by the image classification unit 2b, calculates the position of the feature-image area of each of the detected images-of-interest, and adds the position information that indicates the calculated position to the image-of-interest. The image-of-interest selector 12e detects the position changes of the image areas corresponding to each of the feature-image area and the surrounding area of the feature-image area generated between the temporally continuous images-of-interest, and selects the representative image-of-interest that represents a plurality of similar images-of-interest. The representative-image extracting unit 2d extracts the representative image-of-interest and the first image as the representative images from each of the image groups, sets the display rates for each of the extracted representative images. The image display controller 6a sequentially displays the series of representative images based on the set display rates. Accordingly, it becomes possible to exclusively display the images that have no similarity between the temporally sequential images and for which the observation is highly required, from among the images including the bleeding sites. Further, it becomes possible to reduce the display time by exclusively displaying the first image of each of the image groups instead of displaying the images that do not include the bleeding sites, show a normal state, and for which the observation is less required. As a result, the series of images can effectively be observed.

According to the first and the second embodiments described above, it is described that the series of images that are not grouped are firstly read and then various processes are performed. However, it is acceptable to read the image that is previously associated with the group number, the image-of-interest information, and the display rate, and to execute each of the processes to update each of the information, through the same process procedures.

Further, according to the first and the second embodiments described above, the image display controller 6a sequentially displays the series of representative images from the temporally first image, and displays all the sequential representative images. However, it is acceptable to start displaying a representative image temporally in the middle order, based on instruction information related to a previously input display-initializing image, and to terminate the image display process by displaying until a representative image temporally in the middle order, based on instruction information related to a previously input display-terminating image.

Further, according to the first and the second embodiments described above, it is described that the image display controller 6a exclusively displays the representative image. However, it is acceptable to make it possible to switch a mode for exclusively displaying the representative image and for displaying all the images, based on instruction information input from a predetermined switch.

Moreover, according to the first embodiment described above, it is configured that the control unit 6 performs the image-of-interest detection process after the grouping process is performed. However, it is acceptable that the grouping process is performed after the image-of-interest detection process. Similarly, according to the second embodiment, it is acceptable that the control unit 6 performs the grouping process after the image-of-interest detection process or the image-of-interest selection process is performed.

INDUSTRIAL APPLICABILITY

As described above, the image display apparatus according to the present invention is suitable for the image display apparatus that sequentially displays a series of input images, and more specifically, for the image display apparatus that displays a series of intra-subject images captured by using a capsule endoscope.

The invention claimed is:

1. An image display apparatus that sequentially displays a series of input images, the image display apparatus comprising:
   an image processor comprising hardware, the image processor executing:
   an image classification unit that classifies each of images included in the series of images into two or more image groups, including one or more temporally consecutive images, based on a correlation level among each of the images;
   a feature-image detector that detects a feature-image area including a predetermined feature from each of the images, and detects each of feature images including the detected feature-image area from the series of images;
   a representative-image extracting unit that extracts each of the feature images included in each of the two or more image groups as one or more representative images that represent each of the two or more image groups when each of the two or more image groups includes at least one feature image, and extracts one image based on a predetermined criteria as a representative image from each of the two or more image groups when each of the two or more image groups does not include a feature image;
   a feature-image selector that calculates a variation amount of a predetermined feature amount of the feature-image area generated between the temporally continuous feature images from among a plurality of the feature images detected by the feature-image detector, and selects a feature-representative image that represents a plurality of the feature images based on the calculated variation amount; and
   an image display controller comprising hardware that performs a control of sequentially displaying the representative images extracted by the representative-image extracting unit one by one in a temporal order by displaying the representative image which is a feature image at a slow-display rate and displaying the representative image which is not a feature image at a normal-display rate which is faster than the slow-display rate; wherein
   the feature-image detector calculates the predetermined feature amount of each of the detected feature-image areas,
   the feature-image selector calculates the variation amount based on the feature amount calculated by the feature-image detector,
   the representative-image extracting unit extracts the feature-representative image as the representative image from among the feature images in each of the image groups, and
   the predetermined feature amount is a position of the feature-image area in the feature-image.

2. The image display apparatus according to claim 1, wherein the image display controller performs a control of displaying a mark indicating the feature image in a neighborhood of the representative image, when the representative image of the feature image is displayed.

3. The image display apparatus according to claim 1, wherein
   each of the images is a captured image of an inside of organs, and
   the predetermined feature is a feature that indicates a lesion of the inside of the organs.

4. The image display apparatus according to claim 3, wherein the feature that indicates the lesion is at least one of a bleeding, a discoloration, and a shape anomaly.

5. The image display apparatus according to claim 1, wherein the series of images is generated by using a capsule endoscope.

6. The image display apparatus according to claim 1, wherein the representative-image extracting unit extracts, as the representative image of each of the two or more image groups, a temporally first image in each of the two or more image groups, a temporally last image in each of the two or more image groups, or an image in a predetermined order in each of the two or more image groups when each of the two or more image groups does not include the feature image.

* * * * *